US010080714B2

(12) United States Patent
Idkowiak-Baldys et al.

(10) Patent No.: US 10,080,714 B2
(45) Date of Patent: Sep. 25, 2018

(54) PEPTIDES AND THEIR USE IN THE TREATMENT OF HAIR

(71) Applicant: Avon Products, Inc., Suffern, NY (US)

(72) Inventors: Jolanta Idkowiak-Baldys, Montebello, NY (US); Uma Santhanam, Tenafly, NJ (US)

(73) Assignee: Avon Products, Inc., Rye, NY (US)

( * ) Notice: Subject to any disclaimer, the term of this patent is extended or adjusted under 35 U.S.C. 154(b) by 0 days.

(21) Appl. No.: 15/192,078

(22) Filed: Jun. 24, 2016

(65) Prior Publication Data

US 2017/0143604 A1    May 25, 2017

Related U.S. Application Data

(60) Provisional application No. 62/257,366, filed on Nov. 19, 2015.

(51) Int. Cl.
| | |
|---|---|
| *A61K 8/64* | (2006.01) |
| *A61Q 7/00* | (2006.01) |
| *A61Q 5/12* | (2006.01) |
| *A61Q 5/00* | (2006.01) |

(52) U.S. Cl.
CPC ............... *A61K 8/64* (2013.01); *A61Q 5/00* (2013.01); *A61Q 5/12* (2013.01); *A61Q 7/00* (2013.01); *A61K 2800/57* (2013.01)

(58) Field of Classification Search
CPC ........ A61K 8/64; A61K 2800/57; A61Q 5/00; A61Q 7/00; A61Q 5/12
See application file for complete search history.

(56) References Cited

U.S. PATENT DOCUMENTS

| | | | |
|---|---|---|---|
| 7,186,754 B2 * | 3/2007 | Kaddurah-Daouk | A61K 8/44 424/401 |
| 8,263,053 B2 * | 9/2012 | Duvel | A61K 8/44 424/70.1 |
| 2013/0064905 A1 * | 3/2013 | Duggan | A61K 38/06 424/725 |

FOREIGN PATENT DOCUMENTS

| | | | | |
|---|---|---|---|---|
| JP | 56115708 | * | 9/1981 | ............... A61K 7/00 |
| WO | WO 2016/006733 A1 | * | 1/2016 | ............ A61K 38/06 |

OTHER PUBLICATIONS

Corticotropin-sei whale, from https://www.ncbi.nlm.nih.gov/protein/ 54036887, pp. 1-3, accessed Jun. 22, 2017.*
Ribosomal protein S27-Methanothermobacter thermautotrophicus, from https://www.ncbi.nlm.nih.gov/protein/2622414, pp. 1-3, accessed Jun. 22, 2017.*
Water, from http://www.biology-online.org/dictionary/Water, pp. 1-3, acccessed Apr. 24, 2014.*
Nature Source of Creatine, from http://www.livestrong.com/article/ 440009-what-is-a-natural-source-of-creatine/, Apr. 15, 2015, pp. 1-2.*
English translation of WO2016/006733 A1, pp. 1-9, accessed Jun. 21, 2017.*
English translation of JP 56115708, pp. 1-17, accessed Sep. 2008.*
Cosmetic Emulsifying Agents, from http://www.thegoodscentscompany. com/cosdata/emulsifying.html, pp. 1-127, accessed Jun. 22, 2017.*
Li et al, Autologous Platelet-Rich Plasma: A Potential Therapeutic Tool for Promoting Hair Growth, Dermatol Surg, 2012, 38, pp. 1040-1046.*
Fu et al, Biological fate of amino acid, peptide and protein hydroperoxides, Biochem. J., 1995, 311, pp. 821-827.*

* cited by examiner

*Primary Examiner* — Julie Ha
*Assistant Examiner* — Li N Komatsu
(74) *Attorney, Agent, or Firm* — Brian P. McCloskey

(57) ABSTRACT

Peptides, topical compositions, and methods of improving health and/or appearance of human integuments, such as keratinous surfaces and fibers are provided. The peptides have from 3-12 amino acid residues and comprise the sequence YNT (SEQ ID NO: 1) or PVG (SEQ ID NO: 2).

15 Claims, No Drawings
Specification includes a Sequence Listing.

PEPTIDES AND THEIR USE IN THE TREATMENT OF HAIR

CROSS-REFERENCE TO RELATED APPLICATION

This patent application claims priority to U.S. patent application Ser. No. 62/257,366, filed on Nov. 19, 2015. The entirety of the aforementioned application is incorporated herein in its entirety by reference.

SEQUENCE LISTING

The instant application contains a Sequence Listing which has been submitted electronically in ASCII format and is hereby incorporated by reference in its entirety. Said ASCII copy, created on Jun. 23, 2016, is named HC29U-US_SL.txt and is 2,904 bytes in size.

FIELD OF INVENTION

The present invention relates generally to peptides and derivatives thereof, topical formulations containing them, as well as associated methods for treating human keratin fibers. In particular, the peptides of the invention improve the health and appearance of keratin fibers, strengthen keratin fibers, and promote grown and thickening of keratin fibers.

BACKGROUND

Consumers continually seek to improve the appearance of their hair. Hair loss and thinning are problems that afflict both men and women, and may be associated with low self-esteem and self-consciousness, and therefore can have a negative impact on general quality of life. Various approaches have attempted to prevent keratin fiber loss and thinning, and to enhance the growth, fullness, and appearance of keratin fibers, but these have been largely unsuccessful. Accordingly, there remains a need for effective keratin fiber care products that can address the problems of poor keratin fiber appearance, keratin fiber loss, slowed keratin fiber growth, and the thinning of keratin fibers.

It is therefore an object of the invention to provide new peptides and compositions containing them. It is also an object of the invention to provide methods for improving the health and/or appearance of hair, thickening hair, and/or promoting hair growth with compositions comprising effective amounts of a peptide of the invention.

The foregoing discussion is presented solely to provide a better understanding of the nature of the problems confronting the art and should not be construed in any way as an admission as to prior art.

SUMMARY OF THE INVENTION

In accordance with the foregoing objectives and others, the present invention provides peptides for provided benefits to human keratin fibers (e.g., hair of the scalp, eyelashes, etc.) and formulations containing such peptides. The peptides are believed to be useful for improving health and appearance of human keratin fibers and/or promoting growth of human keratin fibers and/or thickening the shaft of keratin fibers and/or strengthening human keratin fibers. The peptides are typically applied to human keratin fibers and/or the follicles of such keratin fibers as topical formulations comprising physiologically acceptable vehicles, including without limitation aqueous serums and emulsions. In some embodiments, the active peptides are capable of stimulating proliferation of human hair germinal matrix (HHGM) cells. In some embodiments, the active peptides of the invention are capable of increasing the production of keratin and keratin-associated proteins (KAP's) in the hair. In some embodiments, the active peptides of the invention are capable of increasing the production of cell adhesion proteins in the desmosome, including without limitation cadherins, such as p-cadherin. Therefore, the peptides of the invention are expected to have a beneficial effect on improving the health and appearance of human hair and lashes (e.g., strengthening hair, thickening hair, promoting hair growth, combatting age-related hair thinning, fortifying hair, protecting hair from breakage, reducing the frizzy or brittle appearance of hair, etc.).

In one aspect of the invention, peptides are provided comprising the amino acid sequence YNT (SEQ ID NO: 1) and/or PVG (SEQ ID NO: 2). The peptides may comprise, for example, from 3-12, or from 3-10, or from 3-8, or from 3-6 amino acid residues. In some embodiments, the peptides of the invention may have the structure of formula (I):

$$R_1\text{-}\Psi^a\text{-}\Phi\text{-}\Psi^b\text{-}R_2 \qquad (I)$$

wherein, $\Phi$ represents either the amino acid sequence YNT (SEQ ID NO: 1) or the amino acid sequence PVG (SEQ ID NO: 2), and $\Psi^a$ and $\Psi^b$ are independently either absent or are selected from naturally occurring and/or non-naturally occurring amino acid or non-proteinogenic amino acid residues or from short peptide sequences comprising from 2-4 (e.g., two, three, or four) naturally occurring and/or non-naturally occurring amino acid residues; and $R_1$ and $R_2$ are independently either absent, or are selected from hydrogen, or a $C_{1-26}$ branched or straight chain hydrocarbon. In some embodiments, $\Psi^a$ is absent. In some embodiments, $\Psi^a$ comprises one, two, or three naturally occurring and/or non-naturally occurring or non-proteinogenic amino acid residues. In some embodiments, $\Psi^b$ is absent. In some embodiments, $\Psi^b$ comprises one, two, or three naturally occurring and/or non-naturally occurring or non-proteinogenic amino acid residues. In some embodiments, $R_1$ and/or $R_2$ are absent. In some embodiments, $R_1$ and/or $R_2$ comprise a fatty chain, including without limitation a $C_{14-18}$ fatty chain, such as a palmitoyl group. In some embodiments, $\Psi^a$ and/or $\Psi^b$ comprise a lysine (K) residue. In one implementation, $\Psi^a$ has the form -$\Psi_1$-$\Psi_2$-, where each of $\Psi_1$ and $\Psi_2$ is independently either absent or is selected from naturally occurring and/or non-naturally occurring or non-proteinogenic amino acid residues. In one implementation, $\Psi^a$ has the form -$\Psi_1$-$\Psi_2$- or -$\Psi_1$-$\Psi_2$-$\Psi_3$-, where each of $\Psi_1$, $\Psi_2$, and $\Psi_3$ is independently either absent or is selected from naturally occurring and/or non-naturally occurring or non-proteinogenic amino acid residues. In one implementation, $\Psi^b$ has the form -$\Psi_4$-$\Psi_5$- or -$\Psi_4$-$\Psi_5$-$\Psi_6$-, where each of $\Psi_4$, $\Psi_5$, and $\Psi_6$ is independently either absent or is selected from naturally occurring and/or non-naturally occurring or non-proteinogenic amino acid residues. For example, one or more of $\Psi_1$ and/or $\Psi_2$ and/or $\Psi_3$ and/or $\Psi_4$ and/or $\Psi_5$ and/or $\Psi_6$ may be a lysine (K) residues, and the remaining $\Psi_1$ and/or $\Psi_2$ and/or $\Psi_3$ and/or $\Psi_4$ and/or $\Psi_5$ and/or $\Psi_6$ may be absent or may be a natural or non-natural or non-proteinogenic amino acid, including amino acids of the form $H_2N\text{—}(CH_2)_q\text{—}CO_2H$ where "q" is an integer from 1-10, including amino valeric acid ("Ava"). In one embodiment, the peptides of the invention will have the formula K-Ava-$\Phi$-K or K-$\Phi$-Ava-K, including $R_1$-K-Ava-YNT-$\Psi^b$-$R_2$ (SEQ ID NO: 7) and $R_1$-K-Ava-PVG-$\Psi^b$-$R_2$ (SEQ ID NO: 8). In some embodiments, the peptides will have the form K-Ava- YNTK (SEQ ID NO: 3) or K-Ava-PVGK (SEQ ID NO: 4), where either, or both, of the N-terminus or carboxy terminus may be modified (e.g., through an amide or ester bond) with $R_1$ and/or $R_2$ (e.g., a biotin or palmitoyl chain).

In another aspect of the invention, formulations are provided comprising physiologically active amounts of the peptides of the invention, including peptides according to formula (I), such as YNT (SEQ ID NO: 1), PVG (SEQ ID NO: 2), K-Ava-YNTK (SEQ ID NO: 3), K-Ava-PVGK (SEQ ID NO: 4), and combinations thereof. The formulations typically comprise a physiologically acceptable vehicle, which may be aqueous or anhydrous, but are typically in the form of an aqueous or alcoholic serum or emulsion (e.g., water-in-oil or oil-in-water). The active peptide may be present in the composition in an amount between about 0.000001% to about 10% (e.g., 0.0001-2% or 0.001-1% or 0.01-0.5%) by weight of the composition. The formulations may further include an additional hair growth agent selected from the group consisting of fibroblast growth factor receptor 1 (FGFR1) inhibitors, 5-alpha-reductase inhibitors, vasodilators, prostaglandin F2-alpha (PGF2α) analogs, microcirculation enhancers, creatine, biotinylated tri-peptide (e.g., N-biotinyl-gly-his-lys), and combinations thereof. The formulations may contain suitable adjuvants such as organic solvents, humectants, emollients, rheology modifiers, stabilizers, and thickeners, gelling agents, waxes, film forming polymers, shine agents, detanglers, skin and hair conditioning agents, emulsifiers, anti-oxidants, botanicals, peptides, amino acids, sunscreens, colorants, fillers, vitamins and minerals, fragrances, pH adjusters, chelating agents, preservatives, and the like. The compositions may have the form of a mascara, shampoo, hair rinse, hair conditioner, pomade, hair gel, mousse, hydroalcoholic tonic, cream, spray, emulsion, serum/liquid, or any other form that is suitable for treatment of keratin fibers. The compositions may further comprise additional bioactive agents, such as anti-dandruff agents, antiperspirants, retinoids, alpha-hydroxy acids (e.g., glycolic acid), oxa-acids, salicylic acid, anti-acne agents, ascorbic acid, etc. The additional hair growth agents, bioactive agents, and adjuvants may be present, individually or in the aggregate in amounts from about 0.001% to about 25%, typically from about 0.001% to about 10%, based on the total weight of the composition. The vehicle may comprise from about 1% to about 99.9%, typically from about 5% to about 95% by weight of the composition.

In another aspect, methods are provided for improving health and appearance of human keratin fibers and/or promoting growth of human keratin fibers and/or thickening the shaft of keratin fibers and/or strengthening human keratin fibers. In some embodiments, the keratin fibers are eyelashes. In some embodiments, the keratin fibers are hair of the scalp. In some embodiments, the keratin fibers are hair of the face (e.g., moustache or beard). In some embodiments, the keratin fibers are hair of the scalp that has been damaged, for example, by sun damage, chlorine and other chemicals from swimming pools, bleaching or lightening agents (e.g., peroxide), and/or treatment with colorants (e.g., reactive dyes, such as two-part oxidative dyes). The peptides are typically applied to human keratin fibers and/or to the follicles and/or to the skin surrounding the follicles (e.g., the eyelid or the scalp). Application is typically at least once daily for as long as necessary to achieve the desired results (e.g., at least one, two, four, eight, twelve weeks or longer).

These and other aspects of the present invention will become apparent to those skilled in the art after a reading of the following detailed description of the invention, including the illustrative embodiments and examples.

DETAILED DESCRIPTION

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to variously employ the present invention.

All percentages given herein refer to the weight percentages of a particular component relative to the entire composition, including the vehicle, unless otherwise indicated. It will be understood that the sum of all weight % of individual components within a composition will not exceed 100%. Unless otherwise specified, it will be understood that any components of the formulations according to the invention may comprise from about 0.00001% to about 90% by weight, or from about 0.0001% to about 50% by weight, or from about 0.001% to about 25% by weight, or from about 0.01% to about 10% by weight, or from about 0.1% to about 5% by weight of the composition.

All terms used herein are intended to have their ordinary meaning unless otherwise provided. The phrases "physiologically acceptable," "topically acceptable," and "dermatologically acceptable" are used interchangeably and are intended to mean that a particular component is generally regarded as safe and non-toxic for application to a human integument (e.g., skin) at the levels employed. The term "prevent," as used herein, includes delaying, slowing or forestalling the onset of or progression of a particular condition. The phrase "individual in need thereof" refers to a human that could benefit from improved appearance or health of keratin fibers, such as the hair or lashes. In some embodiments, the individual in need thereof is a female.

As used herein, the term "consisting essentially of" is intended to limit the invention to the specified materials or steps and those that do not materially affect the basic and novel characteristics of the claimed invention, as understood from a reading of this specification. For example, a hair growth agent "consisting essentially of" the peptides of formula (I) will exclude effective amounts of additional hair growth agents.

As used herein, a hydrocarbon, alkyl, alkenyl, alkynyl, aryl, aryl-alkyl, alkyl-aryl, heteroaryl, or combination of any of those will have from 1-30 carbon atoms, unless otherwise specified. Any of the hydrocarbon, alkyl, alkenyl, and alkynyl groups disclosed herein, unless otherwise specified, may be straight-chained, branched, and/or cyclic. Any hydrocarbon, alkyl, alkenyl, alkynyl, aryl, aryl-alkyl, alkyl-aryl, or heteroaryl group may be optionally modified with 1-20 or 1-12 or 1-8 or 1-6 or 1-4 heteroatoms selected from halogen, nitrogen, oxygen, and sulfur, or they may be perfluorinated.

The term "amino acid" is intended to include naturally occurring amino acids and non-proteinogenic amino acids as well as non-naturally occurring amino acids and includes any small molecule (MW<1,000 Daltons) having at least one carboxyl group and at least one primary or secondary amine group capable of forming peptide bonds. The term "peptide" is intended to include any molecule comprising at least two amino acids joined by a peptide bond and therefore includes di-peptides, tri-peptides, oligopeptides, and polypeptides having up to about 20 consecutive amino acid residues linked by peptide bonds. The term "peptide" also embraces structures having one or more linkers, spacers, terminal groups or other substituents or modifications which are not amino acids.

Peptides

The peptides of the invention will typically comprise from 3-20 or from 3-12 or from 3-8 or from 3-6 or from 3-4 consecutive amino acids linked together with peptide bonds. The peptides of the invention may comprise, consist essentially of, or consist of the amino acid sequences:

```
                                            (SEQ ID NO: 1)
YNT; and (SEQ ID NO: 2)
PVG; and combinations thereof.
```

"Consisting essentially of" the specified amino acid sequence(s) is intended to mean that additional amino acids may be present at either terminus provided they do not substantially impair or alter the activity of the peptide, as disclosed herein. For example, in embodiments where a peptide "consists essentially of" SEQ ID NOs 1 and/or 2, any additional amino acids may be excluded from the peptide if their inclusion produces a measurable decrease (e.g., greater than 50% reduction) of the beneficial activity, including, without limitation, proliferation of human hair germinal matrix (HHGM) cells, expression of keratin and keratin-associated proteins (KAP) in hair matrix cells, and/or expression of desmosomal components (e.g., cadherins) in hair matrix cells.

In some embodiments, the peptides may comprise one, two, three or more conservative substitutions of amino acids. As used herein, a "conservative substitution" is one in which substitution of one amino acid for another does not impair the function of the peptide, including substitution of an amino acid having a side chain of a certain nature (e.g., acidic, basic, aromatic, aliphatic uncharged, non-polar uncharged, hydrophilic uncharged) by another amino acid having a side chain of the same nature. Examples of conservative substitutions are shown below in Table 11.

TABLE 1

Conservative Substitutions

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

In some embodiments, the peptides of the invention may comprise modified variants of SEQ ID NOs. 1 and 2 wherein at least one (i.e., one, two or three) of the amino acids is replaced by the "D" (dextrorotary) analogue of the natural "L" optical isomer.

In some embodiments the peptides according to the invention will comprise the sequences of SEQ ID NOs. 1 and 2 with an additional amino acid joined by a peptide bond to the N-terminus or carboxy terminus. The active agents according to the invention may comprise, consist essentially of, or consist of the formulas Ω-YNT, YNT-Ω, Ω-PVG, and PVG-Ω, where Ω is a naturally occurring amino acid selected from Alanine, Cysteine, Aspartic acid, Glutamic acid, Phenylalanine, Glycine, Histidine, Isoleucine, Lysine, Leucine, Methionine, Asparagine, Pyrrolysine, Proline, Glutamine, Arginine, Serine, Threonine, Selenocysteine, Valine, Tryptophan, and Tyrosine, in each case, typically in the L optical isomer. In one embodiment, the peptides of the invention comprise, consist essentially of, of consist of the following sequences:

```
                                            (SEQ ID NO. 5)
YNTK; and/or (SEQ ID NO: 6)
PVGK,
``` and derivatives thereof, including without limitation, lipophilic derivatives (e.g., plamitoyl), hydrophilic derivatives (e.g., PEGylated), and biotinylated derivatives thereof. For example, the peptides of the invention can be modified to improve the lipophilicity, stability, or to enhance penetration through the stratum corneum. In some embodiments, the peptides are modified with a fatty acid chain (e.g., $C_{6-22}$), such as palmitoyl. In some embodiments, at least one of the nitrogen atoms in the amide bonds between adjacent amino acids may be methylated to improve metabolic stability. The peptides may also be phosphorylated, for example by forming one or more phosphoserine, phosphothreonine and/or phosphotyrosine residues. The peptides may also be biotinylated or modified with polyalkylene oxide chains (e.g., PEGylated). Peptides of the invention may have one or more additional amino acids joined to the amino and/or carboxyl terminus via peptide bonds.

In some embodiments, the modified peptides will have the structure according to Formula (I):

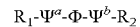

$$R_1\text{-}\Psi^a\text{-}\Phi\text{-}\Psi^b\text{-}R_2 \qquad (I)$$

where Φ represents a peptide sequence of the invention (e.g., comprising SEQ IDs 1 or 2), $R_1$ and $R_2$ are independently either absent or are selected from hydrogen or $C_{1-26}$ ($C_{1-6}$ or $C_{6-12}$ or $C_{12-18}$ or $C_{18-22}$) hydrocarbons (e.g., acyl group, such as palmitoyl), and where $\Psi^a$ and $\Psi^b$ are, independently, absent or are amino acids or peptides (e.g., comprising from 2-6 or from 2-4 or from 2-3 amino acid residues). In some embodiments, $\Psi^a$ and $\Psi^b$ are independently either absent or are selected from naturally occurring and/or non-naturally occurring amino acid or non-proteinogenic amino acid residues or from short peptide sequences comprising from 2-4 (e.g., two, three, or four) naturally occurring and/or non-naturally occurring or non-proteinogenic amino acid residues. In some embodiments, $\Psi^a$ is absent. In some embodiments, $\Psi^b$ is absent. In some embodiments, $\Psi^a$ comprises one, two, or three naturally occurring and/or non-naturally occurring or non-proteinogenic amino acid residues. In some embodiments, $\Psi^b$ comprises one, two, or three naturally occurring and/or non-naturally occurring or non-proteinogenic amino acid residues. In some embodiments, $\Psi^a$ and/or $\Psi^b$ comprises or consists of a lysine (K) residue. In one implementation, $\Psi^b$ has the form -$\Psi_1$-$\Psi_2$-, where each of $\Psi_1$ and $\Psi_2$ is independently either absent or is selected from naturally occurring and/or non-naturally occurring or non-proteinogenic amino acid residues. In one implementation, $\Psi^a$ has the form -$\Psi_1$-$\Psi_2$-$\Psi_3$-, where each of $\Psi_1$, $\Psi_2$, and $\Psi_3$ is independently either absent or is selected from naturally occurring and/or non-naturally occurring or non-proteinogenic amino acid residues. In one implementation, $\Psi^b$ has the form -$\Psi_4$-$\Psi_5$-, where each of $\Psi_4$ and $\Psi_5$ is independently either absent or is selected from naturally occurring and/or non-naturally occurring or non-proteinogenic amino acid residues. In one implementation, $\Psi^b$ has the form $-\Psi_4-\Psi_5-\Psi_6-$, where each of $\Psi_4$, $\Psi_5$, and $\Psi_6$ is independently either absent or is selected from naturally occurring and/or non-naturally occurring or non-proteinogenic amino acid residues. For example, one or more of $\Psi_1$ and/or $\Psi_2$ and/or $\Psi_3$ and/or $\Psi_4$ and/or $\Psi_5$ and/or $\Psi_6$ may be a lysine (K) residue, and the remaining $\Psi_1$ and/or $\Psi_2$ and/or $\Psi_3$ and/or $\Psi_4$ and/or $\Psi_5$ and/or $\Psi_6$ may be absent or may be a natural or non-natural or non-proteinogenic amino acid, including amino acids of the form $H_2N-(CH_2)_q-CO_2H$ where "q" is an integer from 1-10, including amino valeric acid ("Ava"). In some embodiments, $R_1$ and $R_2$ are independently either absent, or are selected from hydrogen, or a $C_{1-26}$ branched or straight chain hydrocarbon. In some embodiments, $R_1$ and/or $R_2$ are absent. In some embodiments, $R_1$ and/or $R_2$ comprise a fatty chain, including without limitation a $C_{14-18}$ fatty chain.

In one embodiment, the peptides of formula (I) will comprise the peptide sequence of formula (II):

$$R_1-\Psi_1-\Psi_2-\Phi-K-R_2 \quad (II)$$

where $\Phi$ represents a peptide sequence of the invention (e.g., comprising SEQ IDs 1 or 2), $R_1$ and $R_2$ are independently either absent or are selected from hydrogen or $C_{1-26}$ ($C_{1-6}$ or $C_{6-12}$ or $C_{12-18}$ or $C_{18-22}$) hydrocarbons (e.g., acyl group, such as palmitoyl), and where each of $\Psi_1$ and $\Psi_2$ is independently either absent or is selected from naturally occurring and/or non-naturally occurring or non-proteinogenic amino acid residues. In some embodiments according to Formula (II), $\Psi_1$ is a naturally occurring amino acid selected from Alanine, Cysteine, Aspartic acid, Glutamic acid, Phenylalanine, Glycine, Histidine, Isoleucine, Lysine, Leucine, Methionine, Asparagine, Pyrrolysine, Proline, Glutamine, Arginine, Serine, Threonine, Selenocysteine, Valine, Tryptophan, and Tyrosine, in each case, typically in the L optical isomer, but optionally in the "D" isomer. In one embodiment, $\Psi_1$ is lysine or a conservative substitution therefor. In one embodiment, $\Psi_2$ is a non-natural or non-proteogenic amino acid.

The non-natural amino acid or non-proteinogenic amino acids used in the peptides of the invention may, for example, have the structures of formula (III) or (IV):

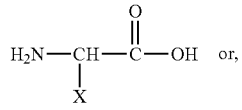

(III)

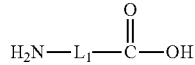

(IV)

where X is selected from $X_1$, $C_{1-26}$ ($C_{1-6}$ or $C_{6-12}$ or $C_{12-18}$ or $C_{18-22}$) hydrocarbons, optionally substituted with a group $X_1$ or with from 1-20 (or 1-10 or 1-6 or 1-3) heteroatoms selected from halogen (e.g., fluorine, chlorine, bromine, iodine), oxygen, nitrogen, phosphorous, sulfur, silicon and combinations thereof. In some embodiments, X is ethyl, propyl, butyl, pentyl, hexyl, heptyl, octyl, nonyl, decyl, undecyl, dodecyl, optionally substituted with $X_1$ or with from 1-20(or 1-10 or 1-6 or 1-3) heteroatoms selected from halogen (e.g., fluorine, chlorine, bromine, iodine), oxygen, nitrogen, phosphorous, sulfur, silicon and combinations thereof. In some embodiments, X is $C_{1-12}$ or $C_{6-20}$ or $C_{12-26}$ alkyl, alkenyl, akynyl, aryl, aryl-alkyl, alkyl-aryl, alkyl-aryl-alkyl, heteroaryl, alkyl-heteroaryl, heteroaryl-alkyl, alkyl-heteroaryl-alkyl, etc., optionally substituted with $X_1$, or with 1-20 (or 1-10 or 1-6 or 1-3) heteroatoms selected from halogen (e.g., fluorine), oxygen, nitrogen, phosphorous, sulfur, and combinations thereof. In some embodiments, X comprises a fused ring system having two, three, or more 5- or 6-membered rings, $X_1$ or with from 1-20 (or 1-10 or 1-6 or 1-3) heteroatoms selected from halogen (e.g., fluorine, chlorine, bromine, iodine), oxygen, nitrogen, phosphorous, sulfur, silicon and combinations thereof. In some embodiments, X, together with the nitrogen atom in Formula (III) forms a 3-13 (e.g., 2-8 or 4-6) membered ring, wherein the amino acid is other than proline.

$L_1$ is a hydrocarbon spacer comprising from 1-20 (or from 2-12 or from 2-8 or from 2-6) carbon atoms and optionally substituted with a group $X_1$ or from 1-20 (or 1-10 or 1-6 or 1-3) heteroatoms selected from halogen (e.g., fluorine, chlorine, bromine, iodine), oxygen, nitrogen, phosphorous, sulfur, silicon and combinations thereof, including perfluorinated derivatives of $L_1$. In some embodiments, $L_1$ will comprise a branched, straight chained, or cyclic hydrocarbon. In some embodiments, $L_1$ will have the form $—(CH_2)p-$ where "p" is an integer from 1-20 or from 1-10 or from 2-8 or from 3-6, including embodiments where p is 1, 2, 3, 4, 5, 6, 7, or 8. In some embodiments, $L_1$ will comprise from 1-6 oxo or oxa groups. In some embodiments, $L_1$ will have the form $—(OCH_2CH_2)p-$ or $—(CH_2CH_2O)p-$ where "p" is an integer from 1-20 or from 1-10 or from 2-8 or from 3-6, including embodiments where p is 1, 2, 3, or 4. In one embodiment, the amino acid of formula (IV) is aminoethanoic acid, aminopropionic acid, aminobutyric acid, aminovaleric acid, aminocaproic acid, aminoenanthic acid, aminocaprylic acid, amino pelargonicacid, or aminocapric acid. In one embodiment, $\Psi_1$ and/or $\Psi_2$ comprises aminovaleric acid. In one embodiment, one of $\Psi_1$ and/or $\Psi_2$ comprises aminovaleric acid and the other comprises lysine (K) joined by a peptide bond to the aminovaleric acid. In some embodiments, $\Psi_2$ is an amino acid of the form $H_2N—(CH_2)_q—CO_2H$ where "q" is an integer from 1-10 or 2-8 or 3-6, including amino valeric acid. In some embodiments, $-\Psi_1-\Psi_2-$ is lysine-amino valeric acid (-K-Ava-).

In some embodiments, $R_1$ and $R_2$ are hydrogen (i.e., they are absent). In some embodiments, one of $R_1$ and $R_2$ is a $C_{1-26}$ hydrocarbon, optionally substituted with a group $X_1$ or from 1-20 (or 1-10 or 1-6 or 1-3) heteroatoms selected from halogen (e.g., fluorine, chlorine, bromine, iodine), oxygen, nitrogen, phosphorous, sulfur, silicon and combinations thereof, including perfluorinated derivatives. In some embodiments, $R_1$ and/or $R_2$ may comprise a straight chained, branched, or cyclic hydrocarbon group. In some embodiments, only one of $R_1$ and $R_2$ is a $C_{1-26}$ (or $C_{2-24}$ or $C_{4-22}$ or $C_{6-20}$ or $C_{12-18}$) hydrocarbon and the other is absent (or is hydrogen). In some embodiments, one of $R_1$ and $R_2$ is a $C_{1-26}$ hydrocarbons selected from the group consisting of alkyl, alkenyl, alkynyl, aryl, alkyl-aryl (e.g., benzyl), and aryl-alkyl optionally substituted with 1-20(or 1-10 or 1-6 or 1-3) heteroatoms selected from halogen (e.g., fluorine), oxygen, nitrogen, phosphorous, sulfur, and combinations thereof, and perfluorinated derivatives thereof. In some embodiments, $R_1$ and/or $R_2$ may comprise a group of the form $R^a—(C=O)—$, where $R^a$ is a $C_{1-25}$ (or $C_{2-24}$ or $C_{4-22}$ or $C_{6-20}$ or $C_{12-18}$) hydrocarbon (e.g., straight chain or branched alkyl) as described above. In one embodiment, $R_1$ and/or $R_2$ may comprise an acyl group, for example, one having the form $CH_3—(CH_2)n-(C=O)—$ where "n" is an integer from 0-25 (e.g., zero or from 1-24 or 2-22 or 10-20 or 12-16), including embodiments where n is 10, 11, 12, 13, 14, 15, or 16. In one embodiment, $R_1$ and/or $R_2$ may comprise an acetyl group of the form $CH_3$—(C=O)—. In one embodiment, $R_1$ and/or $R_2$ may comprise a palmitoyl group of the from $CH_3$—$(CH_2)_{14}$—(C=O)—. $R_1$ and/or $R_2$ may be attached to a nitrogen atom on the peptide so as to thereby form an amide bond of the form Ω-NH—(C=O)—$R^a$, formed, for example, through the reaction of an acid of the form $R^a$-(C=O)—OH (or activated derivative of the acid) with a nitrogen atom on the N-terminal amino group of the peptide or a nitrogen atom on a side chain (e.g., lysine) of the peptide. In some embodiments, $R_1$ and/or $R_2$ may be attached to the peptide through an amide bond of the form Ω-(C=O)—NH—$R^b$, formed, for example, by reaction of an amine of the form $R^b$—NH with the carboxyl terminus of the peptide or on a carboxyl-containing side chain (e.g., aspartic acid or glutamic acid) where $R^b$ can be any of the groups defined for $R^a$. In some embodiments, $R_1$ and/or $R_2$ may be attached to the peptide through an ester bond of the form Ω-(C=)—O—$R^b$, formed, for example, through the reaction of an alcohol of the form $R^b$—OH with the carboxyl terminus of the peptide or carboxyl side chain (e.g., aspartic acid or glutamic acid). In some embodiments, $R_1$ and/or $R_2$ may be attached to the peptide through an ester bond of the form Ω-O—(C=O)—$R^b$, formed, for example, by the reaction of an acid of the form $R^a$—(C=O)—OH with a hydroxyl group on an amino acid side chain (e.g., serine or threonine). In any case where an acid is reacted, the acid may first be activated according to conventional practice by first converting it to an anhydride, acid halide, or activated ester, such as an N-hydroxysuccinimide ester, etc. It is contemplated that $R_1$ and/or $R_2$ may be attached to the peptide through thioester bonds of the form Ω-S—(C=O)—$R^a$, thioether bonds of the form Ω-S—$R^b$, ether bonds of the form Ω-O—$R^b$, and amines of the form of the form Ω-$NR^N$—$R^b$, to name but a few non-limiting example. In various embodiments, $R^a$ and $R^b$ may be branched (e.g., ethylhexyl, isoalkyl, etc.), cyclic, or straight chained. $R^a$ and $R^b$ and $R^N$ may be, without limitation methyl, ethyl, propyl, butyl, pentyl, hexyl, heptyl, octyl, nonyl, decyl, undecyl, dodecyl, or $C_{13}$, or $C_{14}$, or $C_{15}$, or $C_{16}$, or $C_{17}$, or $C_{18}$, or $C_{19}$, or $C_{20}$, or $C_{21}$, or $C_{22}$, or $C_{23}$, or $C_{24}$, or $C_{25}$, or $C_{26}$ alkyl, akenyl (having one, two, three or more double bonds in the cis and/or trans configuration), or akynyl, etc. Any of the groups $R^a$, $R^b$, $R_1$, $R_2$ and $R^N$ may be further substituted with from 1-3 groups $X_1$ or with from 1-20 (or 1-10 or 1-6 or 1-3) heteroatoms selected from halogen (e.g., fluorine), oxygen, nitrogen, phosphorous, sulfur, and combinations thereof.

Optional substituent $X_1$ is selected independently at each occurrence from hydrogen, —F; —Cl; —Br; —I; —OH, —OR*; —NH$_2$; —N(R*)$_2$; —N(R*)$_3$$^+$; —N(R*)—OH; —N(→O)(R*)$_2$; —O—N(R*)$_2$; —N(R*)—O—R*; —N(R*)—N(R*)$_2$; —C=N—R*; —N=C(R*)$_2$; —C=N—N(R*)$_2$; —C(=NR*)—N(R*)$_2$; —SH; —SR*; —CN; —NC; —(C=O)—R*; —CHO; —CO$_2$H; —CO$_2$—; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —(C=NR)—O—R*; —O—(C=NR*)—R*, —SCN; —NCS; —NSO; —SSR*; —N(R*)—C(=O)—N(R*)$_2$; —N(R*)—C(=S)—N(R*)$_2$; —SO$_2$—R*; —O—S(=O)$_2$—R*; —S(=O)$_2$—OR*; —N(R*)—SO$_2$—R*; —SO$_2$—N(R*)$_2$; —O—SO$_3$—R*; —O—S(=O)—R*; —O—S(=O)—OR*; —O—S(=O)—R*; —S(=O)—OR*; —S(=O)—OR*; —S(=O)—R*; —NO; —NO$_2$; —NO$_3$; —O—NO; —O—NO$_2$; —N$_3$; —N$_2$—R*; —N(C$_2$H$_4$); —Si(R*)$_3$; —CF$_3$; —O—CF$_3$; —PR*$_2$; —O—P(=O)(OR*)$_2$; —P(=O)(OR*)$_2$; $C_1$-$C_8$ perfluoroalkyl; an aliphatic $C_1$-$C_8$ hydrocarbon radical; a $C_1$-$C_8$ aromatic hydrocarbon radial; or a $C_1$-$C_8$ heterorayl radical. R* is a $C_{1-10}$ hydrocarbon, such as methyl, ethyl, propyl, butyl, pentyl, hexyl, benzyl, phenyl, etc. Any two of R, R*, $R^N$, $R_1$, and $R_2$ may together form a 3-8 membered, optionally heterocyclic ring.

In some embodiments, $R_1$ and $R_2$ is attached covalently to the terminal carboxyl group. In some embodiments, $R_1$ and/or $R_2$ is attached covalently to the terminal amino group. In some embodiments, $R_1$ and/or $R_2$ is attached to a side chain having a nitrogen, oxygen, or sulfur atom. In some embodiments, the terminal amino groups of the peptides contain one or two methyl groups covalently attached thereto. In one embodiment the terminal carboxyl group is esterified with methanol or ethanol to form a methyl or ethyl ester.

In some embodiments, $R_1$ and/or $R_2$ promotes adhesion to or penetration of an integument. For example, polyarginine (n=2-15 or 2-6) may be beneficially used to enhance penetration of the peptide into skin. In some embodiments, $R_1$ and/or $R_2$ comprise biotin (e.g., attached through the carboxy functionality of the biotin molecule to form an amide bond with the N-terminus of the peptide), or a keto-ester such as a beta-keto ester. The peptide can be PEGylated to enhance water-solubility. In some embodiments, $R_1$ and/or $R_2$ have the form —(OCH$_2$CH$_2$)y—Z or —(CH$_2$CH$_2$O)y-Z, where "y" is an integer from 1-20 (or from 1-10 or from 1-6 or from 1-3) and Z is H, $R_3$, $X_1$, or $R_4$—$X_1$, where $R_3$ and $R_4$ are independently branched, straight chained, or cyclic $C_{1-6}$ hydrocarbons (e.g., methyl, ethyl, propyl, methylene, —(CH$_2$)$_n$- (n=1-6), etc.). In some embodiments, $R_1$ and/or $R_2$ comprise mini-PEG (i.e., 11-amino-3,6,9-trioxaundecanoic acid).

In some embodiments, the peptides will comprise a hydrocarbon chain on the amino and/or carboxyl terminus, including, without limitation, $C_{1-24}$ or $C_{6-18}$ or $C_{12-8}$ aliphatic hydrocarbons, which may be straight chained or branched or cyclic. In some embodiments, the peptides include the reaction product of a peptide with a fatty acid or fatty alcohol. A fatty acid or alcohol, as used herein, contains 6-26 (or 12-18) carbon atoms. For example, the N-terminus may be reacted with a $C_{6-24}$ fatty acid (e.g., palmitic acid) to form an amide bond. The carboxyl terminus may be reacted with a $C_{6-24}$ fatty alcohol (e.g., cetyl alcohol) to form an ester. These fatty derivatives may improve the lipophilicity of the peptide.

In one embodiment, the peptides of the invention will have the structure of formulas (V)-(VIII):

$CH_3$—$(CH_2)_{14}$—(C=O)-YNT     (V)

$CH_3$—$(CH_2)_{14}$—(C=O)-TNY     (VI)

$CH_3$—$(CH_2)_{14}$—(C=O)-PVG     (VII)

$CH_3$—$(CH_2)_{14}$—(C=O)-GVP     (VIII)

where the group —(C=O)— is typically attached to the amino group of the adjacent amino acid.

Topically acceptable salts and prodrugs (collectively "derivatives") of the peptides of the invention are also suitable. Salts will typically be acid addition salts formed by the reaction of the peptide with an inorganic or an organic acid. Inorganic acids include mineral acids such as HCl and H$_2$SO$_4$, and the like. Organic acids include citric, benzoic, tartaric, malic, maleic, succinic, acetic, and propionic acid. The peptides may exist in zwitterionic form. Prodrugs include any esters or amides that hydrolyze in vivo to yield the peptide. Examples of suitable prodrugs can be found in the book entitled "Prodrugs and Targeted Delivery: Towards Better ADME Properties," Volume 47 (2011), published by WILEY-VCH Verlag & Co, which is herein incorporated by reference in its entirety. As used herein, a "prodrug" is a derivative which yields the peptide in vivo, for example through hydrolysis or cleavage of a functional group such as an ester. In one embodiment, the prodrug is formed by reacting the peptide with glyoxylic acid to produce peptidyl-α-hydroxylglycine derivatives having improved stability. In other embodiment the prodrugs may include terminal N-acetyl derivatives, side chain N-acetyl derivatives, N-hydroxy methylation or N-phthalidation of its N-terminus and/or side chain.

It is within the skill in the art to prepare peptides using, for example, conventional protection and activation chemistry. Typically, the amino functionality of a first amino acid is protected with a removable amino protecting group and the carboxyl functionality of a second amino acid is protected with a removable carboxyl protecting group. Suitable amine protecting groups include, without limitation, benzoyloxycarbonyl (Cbz), ter-butoxycarbonyl (t-Boc), and 9-flourenylmethoxycarbonyl (FMOC). The carboxyl group may be protected by forming an acid or base labile ester such as a methyl, ethyl, benzyl, or trimethylsilyl esters. After protection, the first and second amino acids are reacted in a suitable solvent such as water or DMF in the presence of an in situ activating agent such as N,N'-dicyclohexylcarbodiimide (DCCI), diisoproylcarbodiimide (DIPCDI), or 1-ethyl-3-(3'-dimethylaminopropyl)carbodiimide (EDCI) to effect peptide bond formation. Reactive moieties on the side chains of either amino acid are protected with protecting groups such as tert-butyl or benzyl for OH and SH; methyl, ethyl, tert-butyl or benzyl for carboxyl groups, and 2,2,5,7, 8-pentamethylchroman-6-sulphonyl for the —NHC(NH$_2$)=NH functionality of Arg. Following the coupling reaction, selective deprotection of the amino group of the first amino acid is accomplished by acid hydrolysis under conditions that do not remove the carboxyl protecting group of the second amino acid. The procedure is repeated with additional amino protected amino acids. Solid phase synthesis, such as the well-known Merrifield method, is especially useful for synthesizing the peptides of the invention. Lysine-amino valeric acid (K-ava) derivatives are described in U.S. Pat. No. 8,551,956, the disclosure of which is hereby incorporated by reference.

Topical Compositions

The compositions according to the invention may be formulated in a variety of forms for topical application and will typically comprise from about 0.00001% by weight to about 20% by weight of the peptide. More typically, the peptide will comprise from about 0.0001% by weight to about 10% by weight, and more preferably from about 0.001% by weight to about 5% by weight of the composition. In one embodiment, the active peptide or a fragment or derivative thereof will comprise from about 0.001% by weight to about 1% by weight or from about 0.001% by weight or to about 0.1% by weight of the composition. The compositions may comprise an effective amount of the peptide, by which is meant an amount sufficient to stimulate hair matrix cell proliferation, keratin production, KAP production, and/or production of desmonsomal proteins (e.g., cadherins). In other embodiments, the amount of peptide or derivative thereof will be sufficient to promote hair growth and/or thicken the hair shafts and/or strengthen hair when topically applied to the hair and/or scalp daily for a period of at least four, or at least eight weeks.

The peptides of the invention (e.g., comprising any of SEQ ID NOs:1-4) are provided in physiologically acceptable vehicles or carriers. The vehicle may be either hydrophobic or hydrophilic. Suitable, hydrophobic carriers include, for example, hydrocarbons, paraffins, isoparafins, waxes, silicone oils, fatty alcohols, fatty esters and ethers of fatty alcohols and of fatty acids, with carbon chain length from $C_4$ to $C_{22}$, typically from $C_8$ to $C_{18}$, or from $C_{12}$ to $C_{18}$. Examples of fatty hydrophobic carriers include isopropyl myristate, isopropyl pamitate, octyl palmitate, isopropyl lanolate, acetylated lanolin alcohol, the benzoate of $C_{12}$-$C_{15}$ alcohols, cetearyl octanoate, cetyl palmitate, myristyl myristate, myristyl lactate, cetyl acetate, propylene glycol dicaprylate/caprate, decyl oleate, acetylated lanolin, stearyl heptanoate, diisostearyl malate, octyl hydroxystearate, octyl hydroxystearate, isopropyl isostearate, and the like.

Suitable hydrophilic carriers may comprise, for example, water, lower alcohols ($C_{1-6}$) such as ethanol, mixtures of ethanol and water, glycols (e.g., glycerin, propylene glycol, butylene glycol, etc.), and alkoxylated glycols, including ethylene glycol, diethylene glycol, triethylene glycol, propylene glycol, dipropylene glycol, and the like. In one embodiment, the carrier comprises water and/or ethanol.

The physiologically acceptable vehicle may be in the form of an emulsion. Non-limiting example of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions. As used herein, the term "oil" includes silicone oils unless otherwise indicated. The emulsion may include an emulsifier, such as a nonionic, anionic or amphoteric surfactant, or a gellant, typically in an amount from the 0.001% to about 10% by weight.

The vehicle may include water; vegetable oils; mineral oils; ester oils; ethers such as dicapryl ether and dimethyl isosorbide; alcohols such as ethanol and isopropanol; fatty alcohols such as cetyl alcohol, ceterearyl alcohol, stearyl alcohol and behenyl alcohol; isoparaffins such as isooctane, isododecane (IDD) and isohexadecane; silicon oils such as cyclomethicone, dimethicone, dimethicone cross-polymer, polysiloxanes and their derivatives, including PDMS, dimethicone copolyol, dimethiconols, and amodimethiconols; hydrocarbon oils such as mineral oil, petrolatum, isocicosane and polyolefins; e.g., (hydrogenated) polyisobutene; polyols such as propylene glycol, glycerin, butylene glycol, pentylene glycol, hexylene glycol, caprylyl glycol; waxes such as beeswax, carnauba, ozokerite, micorcrystalline wax, polyethylene wax, and botanical waxes; or any combinations or mixtures of the foregoing. Aqueous vehicles may include one or more solvents miscible with water, including lower alcohols, such as ethanol, isopropanol, and the like. The vehicle may comprise, for example, from about 50% to about 99.99% by weight of the composition,more typically from about 75% to about 97.5% by weigh of the composition. In some embodiments, the compositions are anhydrous, by which is meant no water is deliberately added to the formulation. The term "anhydrous" as used herein, does not preclude minor amounts of water that are picked up from the atmosphere or found in trace amounts in the raw ingredients.

In some embodiments, the compositions comprise a penetration enhancer. The penetration enhancer may, for example, be selected from one or more of the group consisting of lower alcohols (e.g., ethanol), fatty alcohols, glycols, polyethylene glycols, fatty acids, fatty esters, fatty ethers, occlusive agents (e.g., waxes, oils, silicones, paraffins, petrolatum, etc.), surface active agents, dimethylaminopropionic acid derivatives, terpenes, sulfoxides, cyclic ethers, amides, urea and amines. Surface active agents include without limitation nonionic, anionic, and cationic agents, and combinations thereof, such as polysorbates, sodium dodecyl sulfate (SDS), macrogol, hydroxystearate, polyvinyl caprolactam-polyvinyl acetate-polyethylene glycol graft co-polymer, lecithin, lysolecithin, nonylphenoxypolyoxyethylene, lysophosphatidyleholine, polyethyleneglycol 400, polyoxyethylene ethers, polyglycol ether surfactants, sodium laurate, sodium lauryl sulfate, cetyltrimethylammonium bromide, docusate sodium, and benzalkonium chloride, etc. Other penetration enhancers that may be useful include dimethylaminopropionic acid derivatives, such as 2-dimethylaminopropionic acid dodecyl ester (DDAIP); terpenes, including terpinolene, limonene, nerol, cineol; sulfoxides such as DMSO; cyclic ethers; amides and amines, such as Didecyldimethylammonium bromide (DDAB), sodium taurodeoxycholate, triethylamine; octyl (e.g., ethylhexyl) salicylate, dimethyl isosorbide, ethoxydigloycol and combinations thereof. Penetrations enhancers may be included in amount from about 0.001-20% by weight. In other embodiments, the peptides may be included in liposomes to improve penetration of the scalp and hair follicle.

The formulations may further include an additional hair growth agent selected from the group consisting of fibroblast growth factor receptor 1 (FGFR1) inhibitors, 5-alpha-reductase inhibitors, prostaglandin F2-alpha (PGF2α) analogs, microcirculation enhancers, creatine, biotinylated tri-peptide (e.g., N-biotinyl-gly-his-lys), aminexil, FP receptor agonists and vasodilators and combinations thereof. Representative additional hair growth agents include aminexil, minoxidil, latanoprost and travoprost. The compositions according to the invention may also optionally comprise one or more 5-alpha reductase inhibitors. Such compounds are known to assist in promotion of hair growth, and include, but are not limited to, saw palmetto (*Serenoa*) extract, *Embilica officianalis* extract, beta-glycyrrhetic acid, estradiol, estrone, progesterone, or asasteroids, such as finasteride and dutasteride. Potassium channel openers, such as Minoxidil, are also contemplated. Saw Palmetto and *Pygeum africanum*. Other agents that may have such activity are beta-sisterol, licorise powder or extract, gamma-linolenic acid and other unsaturated fatty acids, Zinc and Zince salts, green tea catechin (−)-epigallocatechin gallate (EGCG) and other polyphenols, grape and grape seed extracts, etc. Additional hair growth actives, if present, will typically comprise, individually or in the aggregate, from about 0.0001-10% by weight of the formulation.

Other agents that may be optionally added to the compositions of the invention comprise those that act as an exfoliant, such as lactic acid. The composition useful in the methods of the invention may also optionally comprise agents that act on stearoyl coenzyme A desaturase, such as extracts of *Eclipta prostrata*, which is believed to reduce sebum production, thereby improving the health and appearance of, for example, the scalp.

The compositions according to the invention may also optionally comprise one or more vasolators. Use of one or more vasodilation agents can supplement the activity of the peptides and enhance the overall efficacy of the formulation. Examples of useful vasodilation agents include, but are not limited to, arginine, ginseng extracts, gingko extracts, swertia extracts, calpronium chloride, diphenhydramine hycrochloride, gamma-oryzanol, prostaglandins, vitamin E derivatives such as vitamin E nicotinate, pinacidil, minoxidil, phthalides, quina extracts, *Capsicum* extracts, orange peel extracts, and citron extracts. The vasodilators may be used in the compositions of the invention in the amount of about 0.001 to about 10% based on the total weight of the composition.

The compositions according to the invention may also optionally comprise one or more microcirculation enhancers. Apigenin is a citrus-derived flavonoid believed to promote microcirculation when topically applied, and may be included in the compositions of the invention. The compositions according to the invention may also optionally comprise prostaglandin F2α analogs. The compositions useful in the methods of the invention may also optionally comprise creatine. Creatine is a naturally-occuring amino acid derivative that is thought to play a role in cellular energy metabolism. Creatine may be used, for example, use at a concentration of from about 0.01-10% by weight, or from 0.5-1.4 weight % based on the total weight of the composition.

The compositions useful in the methods of the invention may also optionally comprise algae extracts. An algae extract, as used herein, refers to an extract of marine algae. Preferred marine algae include, for example, *Pelvetia canaliculata* and/or *Laminara digitata*. The compositions of the instant invention may comprise an amount of algae extract from about 0.001-10 weight % based on the total weight of the composition, or from about 0.01-3 weight %; or from about 0.02-1 weight %, based on the total weight of the composition. It is believed that the algae extract may also act to maintain healthy structure and function of keratin fiber proteins by stimulating "heat shock proteins" (HSPs). Heat shock proteins (HSPs), also known as "stress proteins," are a family of highly conserved proteins found in all organisms. HSPs are induced by a wide variety of stresses, such as increased temperature, oxygen deprivation, pH changes, chemical insult, UV radiation, and the like. These stresses modify the folding structure of proteins. Improperly folded proteins lead to loss of function and potentially cell death. HSPs bind to proteins during stress to help maintain and/or restore protein structure and function. Without wishing to be bound by theory, it is believed that the algae extract increases activity of HSP27 and HSP70 at the gene level, thereby further protecting keratin fiber proteins, especially during periods of stress. Stresses to keratin fibers may include, for example, stresses from curling the keratin fibers, heat, brushing or combing hair, and shampping and conditioning hair. Suitable agents for modulating HSPs include, for example, *Gynostemma*, coconut water, *Azadiracta*, and *Rhodenta*, described, for example, in U.S. Published Patent Application US2005/0147578, the contents of which are herein incorporated by reference.

The composition of the invention may optionally further comprise one or more cell differentiation activators. Examples of such agents are extracts of sage, for example clary sage, and/or any differentiation active compounds, such as selareolide, obtainable therefrom. Other example of useful differentiation active compounds are forskolin, 7-dehydrocholesterol, and Vitamin D3 analogs. Specifically, a clary sage fermented extract is commercially available from Avoca/RJ Reynolds. Such agents may be used in the compositions of the invention in the amount of about 0.001 to about 10% based on the total weight of the composition.

The compositions of the invention may also optionally comprise one or more firming components, which promote the support in the basement membrane and dermis to encourage and support the keratin fiber structure. Examples of finning components are compounds that enhance the amount of collagen and/or elastin in the skin, for example, collagenase and or elastase inhibitors, or collagen or elastin synthesis enhancers. Such compounds include, but are not limited to triterpenoid-containing extracts and refined compounds, for example, white birch bark extract, *Mimosa tenuiflora* bark extract, or *Pygenum* (Prunus) *africamum* extract and individual active compounds that may be present in these extracts, including betulinol (betulin), betulinic acid, bowellic acid, ursolic acid, oleanolic acid, oleanol, asiaticoside, asiatic acid, and madagassic acid; phenolic-containing extracts, such as green tea extracts and apple extracts, and compounds contained therein, such as EGCG, ECG, catechins, phenylpropanoids, and phloretin; and Vitamin C and derivatives thereof for enhancing collagen syntheseis. The firming agents may be used in the compositions of the invention in the amount of about 0.001 to about 10% based on the total weight of the composition.

The formulations may include one or more vitamins, including, but not limited to, vitamin A, vitamin B's, such as vitamin $B_3$, vitamin $B_5$, andvitamin $B_{12}$, vitamin C, vitamin K, vitamin E such as alpha, gamma or delta-tocopherol, and derivatives (such as salts and $C_{1-16}$ esters) and mixtures thereof. Vitamins, if present, will typically comprise, individually or in the aggregate, from about 0.0001-10% by weight of the formulation.

In one embodiment of the invention, the compositions may include one or more additional skin actives, including but not limited to, retinoids, botanicals, keratolytic agents, dequamating agents, keratinocyte proliferation enhancers, collagenase inhibitors, elastase inhibitors, depigmenting agents, anti-inflammatory agents, steroids, anti-acne agents, antioxidants, and advanced glycation end-product (AGE) inhibitors, to name but a few. The amounts of these various ingredients are those conventionally used in the cosmetic field to achieve their intended purpose, and range individually or collectively typically from about 0.001 wt % to about 20 wt % by weight of the composition. The nature of these ingredients and their amounts must be compatible with the production and function of the compositions of the disclosure.

Exemplary anti-aging components include, without limitation, botanicals (e.g., *Butea frondosa* extract, *Tiliacora triandra* extract, *Portulaca oleracea, Melicope elleryana*, etc.); phytol; phytonic acid; retinoids; hydroxy acids (including alpha-hydroxy acids and beta-hydroxy acids), salicylic acid and alkyl salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); and barrier function enhancing agents (e.g., ceramides, glycerides, cholesterol and its esters, alpha-hydroxy and omega-hydroxy fatty acids and esters thereof, etc.), to name a few.

Exemplary retinoids include, without limitation, retinoic acid (e.g., all-trans, or 9-cis, or 13-cis), and derivatives thereof, retinaldehyde, retinol (Vitamin A) and esters thereof, such as retinyl pamitate, retinyl acetate and retinyl propionate, and salts thereof. Particular mention may be made of retinol. When present, the retinoids will typically be included in amounts from about 0.0001% to about 5% by weight, more typically from about 0.01% to about 2.5% by weight, or from about 0.1% to about 1.0% by weight. Compositions according to this embodiment will typically include an antioxidant such as ascorbic acid and/or BHT and/or a chelating agent such as EDTA or a salt thereof (e.g., disodium EDTA) in amounts effective to stabilize the retinoid (e.g., 0.0001%-5%). The composition may include from 0.001-10% by weight pytol.

In another embodiment, the topical compositions of the present invention may also include one or more of the following: a skin penetration enhancer; an emollient, such as isopropyl myristate, petrolarum, volatile or non-volatile silicones oils (e.g., methicone, dimethicone), ester oils, mineral oils, and fatty acid esters; a humectant, such as glycerin, hexylene glycol or caprylyl glycol; a skin plumper, such as palmitoyl oligopeptide, collagen, collagen and/or glycosaminoglycan (GAG) enhancing agents; an exfoliating agent; and an antioxidant.

Suitable exfoliating agents include, for example, alpha-hydroxy acids, beta-hydroxy acids, oxa-acids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. One exemplary exfoliating agent is glycolic acid. When present, the exfoliating agent may comprise from about 0.001% to about 20% by weight of the composition.

Examples of antioxidants that may be used in the present compositions include compounds having phenolic hydroxy functions, such as ascorbic acid and its derivatives/esters; beta-carotene; catechins; curcumin; ferulic acid derivatives (e.g., ethyl ferulate, sodium ferulate); gallic acid derivatives (e.g., propyl gallate); lycopene; reductic acid; rosmarinic acid; tannic acid; tetrahydrocurcumin; tocopherol and its derivatives, including tocopheryl acetate; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. In one embodiment, the composition comprises thiodipropionic acid or a mono- or diester thereof such as dilauryl thiodipropionic acid. Antioxidants may comprise, individually or collectively, from about 0.001% to about 10% (w/w), or from about 0.01% to about 5% (w/w) of the total weight of the composition.

Other additives include: vitamins, such as tocopherol and ascorbic acid; vitamin derivatives such as ascorbyl monopamitate, tocopheryl acetate, and Vitamine E palmitate; thickeners such as hydroxyalkyl cellulose, carboxymethylcellulose, carbombers, and vegetable gums such as xanthan gum; gelling agents, such as ester-terminated polyester amides; structuring agents; metal chelating agents such as EDTA or salts thereof; fillers and powders, colorants, pH adjusters (citric acid, ethanolamine, sodium hydroxide, etc.); film formers, moisturizers, minerals, viscosity and/or rheology modifiers, anti-acne agents, anti-inflammatories, depigmenting agents, pharmaceutical agents, surfactants, botanicals, sunscreens, insect repellents, skin cooling compounds, skin protectants, conditioners, lubricants, fragrances, excipients, preservatives, stabilizers, emulsifiers, and mixtures thereof. The foregoing may individually or collectively comprise from about 0.0001% to about 20% by weight of the composition.

Details with respect to these and other suitable cosmetic ingredients can be found in the "International Cosmetic Ingredient Dictionary and Handbook," 10th Edition (2004), published by the Cosmetic, Toiletry, and Fragrance Association (CTFA), at pp. 2177-2299, which is herein incorporated by reference in its entirety. The amounts of these various substances are those that are conventionally used in the cosmetic or pharmaceutical fields, for example, they can constitute individually or in the aggregate, from about 0.01% to about 20% of the total weight of the composition.

A sunscreen may be included to protect the skin from damaging ultraviolet rays. The sunscreen may provide both UVA and UVB protection, by using either a single sunscreen or a combination of sunscreens. Among the sunscreens that can be employed in the present compositions are avobenzone, cinnamic acid derivatives (such as octylmethoxy cinnamate), octyl salicylate, homosalate, oxybenzone, octocrylene, titanium dioxide, zinc oxide, or any mixtures thereof. The sunscreen may be present from about 1 wt % to about 30 wt % of the total weight of the composition.

The compositions may include one or more oil-phase and/or water phase gelling agents or thickeners. Hydrophilic gelling agents include carboxyvinyl polymers (carbomer), acrylic copolymers such as acrylate-(alkyl)acrylate copolymers and Acrylates Copolymer (INCI), polyacrylamides, polysaccharides, such as hydroxypropylcellulose, hydroxypropylmethylcellulose, silica, alumina, gums and hydrocolloids, such as xanthan, guar, veegum, carrageenan, gelatin, karaya, pectin and locust beans gum, etc., and clays, and, as lipophilic gelling agents, representative are the modified clays such as bentones, fatty acid metal salts such as aluminum stearates and hydrophobic silica, or ethylcellulose and polyethylene. Other suitable oil-phase gellants include dibutyl lauryl glutamide, dibutyl ethylhexyl glutamide, ethylene block copolymers (ethylene/propylene/butylene block copolymers), polyamides capable of forming a gel with an oil, for example, ester-terminated polyamides (ETPA), ester-terminated poly(ester-amide) polymeric gellants (ETPEA) (e.g., Bis-Stearyl Ethylenediamine/Neopentyl Glycol/Stearyl Hydrogenated Dimer Dilinoleate copolymer (INCI)), tertiary amide terminated polyamides (ATPA), polyalkyleneoxy terminated polyamides (PAOPA), and polyether polyamides (PEPA).

In one embodiment, the topical composition will have a pH range from 1 to 13, with a pH in the range of from 2 to 12 being typical. In some embodiment, the composition will have a pH in the range of from 3.5 to 7 or from 7 to 10.5. In some embodiments, the pH will be in the range of 3-4, or 4-5, or 5-6, or 6-7, or 7-8, or 8-9, or 9-10, or 10-11, or 11-12. Suitable pH adjusters such as sodium hydroxide, citric acid and triethanolamine may be added to bring the pH within the desired range.

Another embodiment of the present disclosure is directed to the delivery of the described compositions by the use of targeted delivery systems, for example, liposomes, microspheres (see e.g., U.S. Pat. No. 5,770,222 to Unger et al.), and the like, so that the components and/or active constituents can more readily reach and affect the subcutaneous layer of the area of application, e.g., face or neck, or the other area of the skin.

The compositions may be formulated in a variety of product forms, such as, for example, a shampoo, conditioner, mousse, hair tonic, styling gel, mascara, lotion, cream, serum, spray, aerosol, cake, ointment, essence, gel, paste, patch, pencil, towelette, mask, stick, foam, elixir, concentrate, and the like, particularly for topical administration. The composition is typically formulated as an emulsion comprising from 0.01-10% by weight of an emulsifier for stabilizing the emulsion.

Methods of Treatment

The invention provides methods for enhancing and/or promoting growth of hair, including hair of the scalp and eyelashes. Methods for thickening hair, including increasing follicle density, are also provided. In some embodiments, the invention provides methods for increasing the diameter of the hair shaft are also provided. In some embodiments, the invention provides methods for increasing the tensile strength of hair fibers. In some embodiments, methods are provided for improving the condition, health, and/or appearance of keratin fibers (e.g., hair of the scalp). Non-limiting examples of improvements in keratin fibers imparted by use of the compositions of the invention comprise: (a) improvement in root sheath thickness; (b) improvement in fiber anchorage; (c) decrease in keratin fiber loss; (d) reduction in keratin fiber breakage; (e) increase in keratin fiber strength; (f) improvement in keratin fiber growth rate; (g) improvement in shine; (h) improvement in the number of visible keratin fibers; (i) improvement in keratin fiber length; and/or (j) improvement in keratin fiber volume. The methods of the invention comprise the step of topically applying the compositions of the invention to the hair and/or scalp and/or area of skin surrounding a hair follicle. The compositions of the invention are preferably applied to affected skin areas once or twice daily for as long as is necessary to achieve desired anti-aging results. The treatment may be at least once or twice daily and may last for a period of at least four weeks, typically at least eight weeks, twelve weeks, or longer. In one embodiment, the compositions of the invention will be applied in an amount from about 0.001 to about 1000 mg/cm$^2$, more typically from about 0.01 to about 200 mg/cm$^2$, or from about 0.1 to about 100 mg/cm$^2$.

In particular, the composition for application to the scalp or hair can be provided in the form of a hair care lotion, for example for daily or twice-weekly application, of a shampoo or of a hair conditioner, in particular for twice-weekly or weekly application, of a liquid or solid soap for cleaning the scalp for daily application, of a product for shaping the hairstyle (lacquer, hair setting product, styling gel), of a treatment mask, of a cream or of a foaming gel for cleaning the hair. It can also be provided in the form of a hair dye or mascara to be applied with a brush or comb.

In some preferred embodiments, a method for stimulating hair growth comprises administering to the skin of a patient, said skin comprising hair follicles, an effective amount of a peptide of the invention, or formulation containing said peptide, wherein the administration causes increased hair growth. The composition may be applied to the scalp. The composition may be applied at least once daily. In some embodiments, the composition is applied to the scalp for treatment of a condition selected from the group consisting of alopecia areata, telogen effluvium, anagen effluvium, cicatricial alopecia, scarring alopecia; hair shaft abnormalities, trichorrexis nodosa, loose anagen syndrome, trichotillomania, traction alopecia; infectious hair disorders, tiniea capitis, seborrheic dermatitis, follicullitus of the scalp, and androgenetic alopecia. In some embodiments, the compositions is applied to one or both of the scalp and the eyebrows, including for patients experiencing hair loss due to chemotherapy, hormonal imbalance, fungal infection of the scalp, anti-coagulants, medicine for gout, depression, high blood pressure and heart disease. In some embodiments, the peptides are applied to slow or arrest the loss of hair.

In another aspect of the invention, the compositions are applied topically to improve the aesthetic appearance of human skin. The method comprises topically applying to an area of the skin in need thereof a composition comprising an effective amount of a peptide of the invention (e.g., comprising any of SEQ ID NOs: 1 or 2) for a time sufficient to improve the aesthetic appearance of said human skin. The composition may optionally further comprise a retinoid (e.g., from 0.0001-5%) and/or alpha-hydroxy acid (e.g., glycolic acid) (e.g., from 0.0001-25%) and/or a beta-hydroxy acid (e.g., salicylic acid or a derivative) (e.g., from 0.0001-15%).

As used herein, "aesthetic improvement" may be measured by evaluation of before and after pictures by panels of dermatologists, or by other objective measures known in the art.

In a related implementation, a method is provided for the treatment of wrinkles and/or fine lines on the skin human skin (typically, skin of the face) comprising topically applying to an area of the skin in the need thereof (e.g., applying to a wrinkle or fine line) a composition comprising a peptide of the invention (e.g., comprising any of SEQ ID NOs: 1-2), for a time sufficient to reduce the visibility, number, or depth of said wrinkles and/or fine lines. The treatment may be a least once or twice daily and may last for a period of at least four weeks, typically at least eight weeks, twelve weeks, or longer. The composition may optionally further comprise a retinoid (e.g., retinol or retinyl palmitate) and/or an alpha-hydroxy acid (e.g., glycolic acid) and/or a beta-hydroxy acid (e.g., salicylic acid or derivative) in amounts effective to improve the appearance of skin. In some embodiments, methods reduce the severity of, reduce the number of, or prevent or forestall the onset of, wrinkles or fine lines on human skin. The composition may be topically applied to an area of the skin in need thereof (e.g., directly to wrinkled skin), an effective amount (e.g., 0.000001%-1% by weight, w/w) of a peptide of the invention (e.g., comprising any of SEQ ID NOs: 1 or 2) in combination with an effective amount (e.g., 0.01%-5% by weight, w/w) of retinol and/or an effective amount (e.g., 0.001%-20% by weight, w/w) of an alpha-hydroxy acid (e.g., glycolic acid) and/or a beta-hydroxy acid (e.g., salicylic acid). The effect of a composition on the formation or appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin).

Topically application of a composition comprising a peptide comprising any of SEQ ID NOs: 1 or 2, typically in a physiologically acceptable vehicle, over an affected area of skin may remediate, reverse, reduce, ameliorate, or prevent dermatological signs of aging. Generally, the improvement in the condition and/or appearance of skin is selected from the group consisting of: reducing dermatological signs of chronological aging, photo-aging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation or hypopigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; slowing or halting skin thinning; increasing skin elasticity and/or resiliency; enhancing exfoliation; improving microcirculation; decreasing and/or preventing cellulite formation; and any combinations thereof. In some embodiments, each of the forgoing is associated with female skin.

The improvement in aesthetic appearance of human skin also may be an improvement of any attribute or characteristic of skin, including without limitation:

(a) treatment, reduction, and/or prevention of fine lines or wrinkles;
(b) reduction of skin pore size;
(c) improvement in skin thickness, plumpness, and/or tautness;
(d) improvement in skin smoothness, suppleness and/or softness;
(e) improvement in skin tone, radiance, and/or clarity;
(f) improvement in procollagen, and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) improvement of skin appearance decreased by aging and/or menopause;
(n) improvement in skin moisturization;
(o) increase in skin elasticity and/or resiliency;
(p) treatment, reduction, and/or prevention of skin sagging;
(q) improvement in skin firmness; and
(r) reduction of pigment spots and/or mottled skin; and
(s) improvement of optical properties of skin by light diffraction or reflection.

It is also contemplated that the compositions of the invention will be useful for treating thin skin by topically applying the composition comprising the active peptides (e.g., comprising any of SEQ ID NOs: 1 or 2) to thin skin of an individual in need thereof. "Thin skin" is intended to include skin that is thinned due to chronological aging, menopause, or photo-damage and skin that is thinning prematurely. In some embodiments, the treatment is for thin skin in men, whereas other embodiments treat thin skin in women, pre-menopausal or post-menopausal, as it is believed that skin thins differently with age in men and women, and in particular in women at different stages of life.

The method of the invention may be employed prophylactically to forestall aging including in individuals that have not manifested signs of skin aging, most commonly in individuals under 25 years of age. The method may also reverse or treat signs of aging once manifested as in common in individuals over 25 years of age, or to slow the progression of dermatological aging in such individuals.

In one embodiment, the compositions of the invention comprising active peptides (e.g., comprising any of SEQ ID NOs: 1 or 2) are applied to human skin to reduce sebum production or improve the appearance of skin affected by cellulite, and/or reduce unwanted lipogenesis or increase lipolysis. In this embodiment, the peptides of the invention can be formulated in topically acceptable vehicles (as described herein) and may include one or more additional agents such as anti-acne ingredients (e.g., salicylic acid, benzoyl peroxide and other peroxides, sulfur, retinoids, etc.) in the case of a facial composition, or, in the case of a cellulite treatment, the formulation may comprise any ingredients suitable for treatment of cellulite, including without limitation, perilla oil and other unsaturated fatty oils and omega-3 fatty acids such as alpha-linolenic acid; caffeine; theophylline; xanthines; retinoids (e.g., retinol); and the like. A cellulite treatment according to the invention will typically be applied topically to skin suffering from cellulite, including skin of the buttocks and thighs for a period of time sufficient to improve the appearance thereof, including for example, daily treatment for at least four weeks, at least eight weeks, at least twelve weeks, or long. In on embodiment, the compositions are topically applied to treat acne.

In certain embodiments, the compositions described herein comprising active peptides (e.g., comprising any of SEQ ID NOs: 1 or 2) can be used to treat and/or prevent hyper-pigmentation of skin and/or of the hair, for example, to lighten skin or hair. In some embodiments, the compositions are topically applied to the skin or hair, for example to an area of hyper-pigmented skin or hair. Hyper-pigmentation includes any coloration of an individual's skin or hair that is darker than desired by the individual and that is caused by melanocytes. Hyper-pigmented areas of the skin include areas of discrete or mottled hyper-pigmentation. Areas of discrete hyper-pigmentation can be distinct, uniform areas of darker color and may appear as brown spots or freckles on the skin, including marks commonly called pigment spots or "age spots." Areas of mottled hyper-pigmentation of the skin can be dark blotches that are larger and more irregular in size and shape than areas of discrete pigmentation. Areas of hyper-pigmentation also includes areas of tanned skin, for example, skin tanned due to UV exposure. Hyper-pigmented hair includes any shade of hair that is darker than desired.

Treating hyper-pigmentation or hyper-pigmented skin/hair refers to eradicating, reducing, ameliorating, or reversing one or more of the unwanted features associated with hyper-pigmentation, such as producing a perceptible lightening of the skin or hair in the affected area. Lightening hyper-pigmented areas of the skin may be effective in diminishing age spots; lightening a suntan; evening or optimizing skin tones, e.g., in areas of mottled hyper-pigmentation; in treating melasmic and chloasmic patches, freckles, after-burn scars, and post-injury hyper-pigmentation. Preventing hyper-pigmentation or hyper-pigmented skin refers to affording skin, not yet affected by hyper-pigmentation, a benefit that serves to avoid, delay, forestall, or minimize one or more unwanted features associated with skin hyper-pigmentation, such as reducing the darkness or size of hyper-pigmented areas that eventually develop.

In some embodiments, the compositions of the invention are used in a rotational, alternating, or sequential treatment regimen comprising topical application of the compositions of the invention for a first period of time (e.g., at least once daily for at least one day), followed by a second period of time in which at least one additional treatment modality is administered for at least one additional day following said first period of time. The second treatment modality may comprise topical application of any hair or skin benefit agent, such as a hair growth agent (e.g., finesteride, Minoxidil, cis-6-nonenol, thiazolylalanine, botanical extracts from *Pouzolzia pentandra*, etc.), retinoid (e.g., retinol), phytol, antioxidants (e.g., ascorbic acid or TDPA or esters thereof), botanicals, such as *Tiliacora triandra*, niacinamide, vitamins such as Vitamin E and Vitamin E acetate, salicylic acid, salicylates and derivatives thereof, moisturizers, emollients, etc.

In another embodiment, the peptides of the invention (e.g., comprising any of SEQ ID NOs: 1 or 2) are intended for oral use, including for pharmaceutical use. Pharmaceutical formulations will include pharmaceutically acceptable carriers (i.e., diluents and excipients). The pharmaceutical compositions may be included in solid dosage forms, including compressed tablets and capsules, or in liquid or powder forms (including lyophilized powders of the peptide suitable for reconstitution with water). Pharmaceutical compositions may also be in the form of creams, serums, etc., or formulated for injection. Pharmaceutical dosage forms will typically include from about 0.1 mg to about 200 mg, or from about 1 mg to about 100 mg of the peptides of the invention. Solid dosage forms may be immediate release, in which case they will typically comprise a water-soluble or dispersible carrier such as microcrystalline cellulose, mannitol, hydroxypropyl methyl cellulose, PVP or the like, or may be delayed, sustained, or modified release, in which case they may comprise water-insoluble polymers such as cellulose ethers (e.g., ethylcellulose), alone or in combination with water soluble or dispersible polymers, to regulate the rate of dissolution of the dosage form in the stomach.

In one embodiment, the composition is intended for use as a non-therapeutic treatment. In another embodiment, the composition is an article intended to be rubbed, poured, sprinkled, or sprayed on, introduced into, or otherwise applied to the human body for cleansing, beautifying, promoting attractiveness, or altering the appearance, in accordance with the US FD&C Act, § 201(i).

EXAMPLES

The following example illustrates a specific aspect of the instant description. The example should not be construed as limiting, as the example merely provides specific understanding and practice of the embodiments and its various aspects.

Example 1

Proliferation of the Hair Matrix Cells

Hair Germinal Matrix Cells (ScienCell, Carlsbad, Calif.) were grown in 96-well tissue culture plate (5000 cells/well) in MSCM medium supplemented with growth factors (ScienCell, Carlsbad, Calif.). Cells were incubated overnight at 37° C. and 5% $CO_2$. Next, media were aspirated and cells were incubated in MSCM medium without growth supplement for 4-6 h, followed by treatment with given concentration of peptides for 24 h. After treatment cells were incubated with BrdU for 4 h and proliferation rate was evaluating using BrdU proliferation kit from Cell Signaling (Danvers, Mass.). The results are summarized in Table 2 below as percent change cell proliferation relative to vehicle control (peptide concentrations provided in parentheses) using the following key: 0: <10%, +:11-20%, ++:21-40%, +++:41-60%, ++++:>60%.

TABLE 2

| Peptide Sequence | Wt. % | Proliferation (%) |
|---|---|---|
| YNT (SEQ ID NO: 1) | 0.0001 | ++ |
|  | 0.00001 | 0 |
| K-Ava-YNTK (SEQ ID NO: 3) | 0.0001 | 0 |
|  | 0.00001 | 0 |
| PVG (SEQ ID NO: 2) | 0.0001 | + |
|  | 0.00001 | 0 |
| K-Ava-PVGK (SEQ ID NO: 4) | 0.0001 | 0 |
|  | 0.00001 | 0 |

As shown in Table 2, tripeptides YNT (SEQ ID NO: 1) and PVG (SEQ ID NO: 2) of the invention effectively increase Hair Germinal Matrix Cell proliferation. Surprisingly, the hydrolytically more stable K-Ava-derivatives of these tripeptides did not have an effect on cell proliferation at the concentrations tested. Based on these results, it is contemplated that tripeptides YNT (SEQ ID NO: 1) and PVG (SEQ ID NO: 2), and lipophilic plamitoyl derivatives thereof, will have benefit in promoting growth of hair, including hair of the scalp and eyelashes, as well as retarding hair loss, and promoting hair shaft thickness.

Example 2

Expression of Keratin, Keratin Associated Proteins (KAPs), P-Cadherin

Hair Germinal Matrix Cells (ScienCell, Carlsbad, Calif.) were grown in 6-well tissue culture plate ($1.5 \times 10^5$ cells/well) in MSCM medium supplemented with growth factors (ScienCell, Carlsbad, Calif.). Cells were incubated overnight at 37° C. and 5% $CO_2$. Next day, cells were changed into fresh media and treated with given concentration of peptides for 48 h. After treatment, cells were washed with ice cold PBS, collected into RLT lysis buffer and RNA was extracted using RNeasy Mini Kit (Qiagen, Valencia, Calif.) following manufactures recommendations. 200 ng of RNA was used for cDNA synthesis using High Capactiy cDNA Reverse Transcription Kit (Life Technologies, Carlsbad, Calif.). 1 µL of undiluted cDNA was used per qPCR reaction. Primers used were purchased from Life technologies (Carlsbad, Calif.). Following primers were used: Keratin35 (Hs0060557_g1), KAP8 (Hs00545666_s1), KAP11 (Hs00545667_s1), P-cadherin (Hs00999925_m1). Expression was normalized to GAPDH. The conditions of q-PCR were: an incubation step at 50° C. for 2 minutes and an enzyme activation step at 95° C. for 10 minutes; followed by 45 cycles of 95° C. for 30 seconds and 60° C. for 1 minute. CT value was obtained from the software of the Stratagene MX2005P. These results are summarized in Table 2 below as percent change in mRNA expression relative to vehicle control using the following key: 0; <10%, +: 11-20%, ++: 21-40%, +++: 41-60%, ++++: >60%

TABLE 3

| Peptide Sequence | Wt. % | Keratin 35 | KAP 8 | KAP 11 | P-cadherin |
|---|---|---|---|---|---|
| YNT (SEQ ID NO: 1) | 0.0001 | 0 | ++++ | ++++ | + |
| K-Ava-YNTK (SEQ ID NO: 3) | 0.0001 | 0 | 0 | 0 | +++ |
| PVG (SEQ ID NO: 2) | 0.0001 | 0 | ++++ | 0 | 0 |
| K-Ava-PVGK (SEQ ID NO: 4) | 0.0001 | +++ | ++++ | +++ | 0 |

As shown in Table 2, tripeptides YNT (SEQ ID NO: 1) and PVG (SEQ IDNO: 2) of the invention effectively increase mRNA expression for Keratin Associated Protein 8. Interestingly, the hydrolytically more stable K-Ava-derivative K-Ava-PVGK (SEQ ID NO: 4) was effective in upregulating expression of mRNA for Keratin 35, KAP8 and KAP11, whereas the K-Ava-derivative K-Ava-YNTK (SEQ ID NO: 3) was not effective at the concentration tested. Tripeptide YNT (SEQ ID NO: 1) was effective in boosting levels of the desmosomal protein P-cadherein. The effect was enhanced in the K-Ava-derivative K-Ava-YNTK (SEQ ID NO: 3).

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings. Accordingly, the present description is intended to embrace all such alternatives, modifications, and variances which fall within the scope of the appended claims.

The invention claimed is:

1. A topical composition for improving the health and/or appearance of hair, thickening hair, and/or promoting hair growth comprising
an active agent selected from YNT (SEQ ID NO: 1), K-Ava-YNTK (SEQ ID NO: 3), or palmitoyl-YNT, and a physiologically acceptable vehicle,
wherein the active agent is present in an amount from 0.0001% to 10% by weight of the composition.

2. The topical composition according to claim 1, wherein said active agent consists of said peptide optionally functionalized with a $C_{2-24}$ hydrocarbon.

3. The topical composition according to claim 2, wherein said active agent is palmitoyl-YNT.

4. The topical composition according to claim 1, wherein said active agent is K-Ava-YNTK (SEQ ID NO: 3).

5. The topical composition of claim 1, wherein the active agent is present in an amount from 0.001% to 1% by weight of the composition.

6. The topical composition of claim 1, wherein said physiologically acceptable vehicle comprises a water-in-oil, oil-in-water, silicone-in-water, or water-in-silicone emulsion.

7. The topical composition of claim 1, wherein said composition is in the form of shampoo, conditioner, hair gel, mousse, tonic, or lotion.

8. The topical composition of claim 1, wherein said composition further comprises one or more ingredients selected from the group consisting of creatine, a botanical extract from *Pouzolzia pentandra*, N-biotinyl-gly-his-lys, hydrolyzed wheat protein, saw palmetto extract, *Emblica officianalis* extract, and beta-glycyrrhetic acid.

9. The topical composition of claim 1, wherein said active agent is YNT (SEQ ID NO: 1), or K-Ava-YNTK (SEQ ID NO: 3).

10. The topical composition of claim 1, wherein said active agent is YNT (SEQ ID NO: 1).

11. A method for strengthening, thickening, and/or promoting growth of human keratin fibers, wherein the method comprises topically applying the topical composition according to claim 1 to the skin in the area of keratin fiber follicles.

12. The method according to claim 11, wherein said active agent consists of said peptide optionally functionalized with a $C_{2-24}$ hydrocarbon to improve lipophilicity.

13. The method according to claim 11, wherein said active agent is palmitoyl-YNT.

14. The method according to claim 11, wherein said active agent is K-Ava-YNTK (SEQ ID NO: 3).

15. The method according to claim 11, wherein said composition is applied at least once daily for at least four weeks.

\* \* \* \* \*

SEQUENCE LISTING

<160> NUMBER OF SEQ ID NOS: 8

<210> SEQ ID NO 1
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Tyr Asn Thr
1

```
<210> SEQ ID NO 2
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Val Gly
1

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Amino valeric acid

<400> SEQUENCE: 3

Lys Xaa Tyr Asn Thr Lys
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Amino valeric acid

<400> SEQUENCE: 4

Lys Xaa Pro Val Gly Lys
1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Asn Thr Lys
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Pro Val Gly Lys
1
```

```
<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (6)..(9)
<223> OTHER INFORMATION: Any naturally occurring, non-naturally
      occurring or non-proteinogenic amino acid residue
<220> FEATURE:
<221> NAME/KEY: MISC_FEATURE
<222> LOCATION: (6)..(9)
<223> OTHER INFORMATION: This region may encompass 1 to 4 amino acids
      wherein some positions may be absent
<220> FEATURE:
<223> OTHER INFORMATION: See specification as filed for detailed
      description of substitutions and preferred embodiments

<400> SEQUENCE: 7

Lys Xaa Tyr Asn Thr Xaa Xaa Xaa Xaa
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (6)..(9)
<223> OTHER INFORMATION: Any naturally occurring, non-naturally
      occurring or non-proteinogenic amino acid residue
<220> FEATURE:
<221> NAME/KEY: MISC_FEATURE
<222> LOCATION: (6)..(9)
<223> OTHER INFORMATION: This region may encompass 1 to 4 amino acids
      wherein some positions may be absent
<220> FEATURE:
<223> OTHER INFORMATION: See specification as filed for detailed
      description of substitutions and preferred embodiments

<400> SEQUENCE: 8

Lys Xaa Pro Val Gly Xaa Xaa Xaa Xaa
1               5
```